US006376179B1

(12) United States Patent
Laayoun

(10) Patent No.: US 6,376,179 B1
(45) Date of Patent: Apr. 23, 2002

(54) PROCESS FOR LABELING A RIBONUCLEIC ACID, AND LABELED RNA FRAGMENTS WHICH ARE OBTAINED THEREBY

(75) Inventor: Ali Laayoun, Lyons (FR)

(73) Assignee: Bio Merieux, Marcy l'Etoile (FR)

( * ) Notice: Subject to any disclaimer, the term of this patent is extended or adjusted under 35 U.S.C. 154(b) by 0 days.

(21) Appl. No.: 09/446,156

(22) PCT Filed: Jun. 17, 1999

(86) PCT No.: PCT/FR99/01469

§ 371 Date: Dec. 17, 1999

§ 102(e) Date: Dec. 17, 1999

(87) PCT Pub. No.: WO99/65926

PCT Pub. Date: Dec. 23, 1999

(30) Foreign Application Priority Data

Jun. 17, 1998 (FR) ........................................... 98 07870

(51) Int. Cl.[7] .......................... C12Q 1/68; C12P 19/34; C07H 21/00; C07D 225/00; C07F 7/24

(52) U.S. Cl. ......................... 435/6; 435/91.2; 536/25.3; 536/25.31; 536/25.32; 540/465; 540/474; 556/1; 556/6

(58) Field of Search .................. 435/6, 91.2; 536/25.3, 536/25.31, 25.32; 540/474, 465; 556/1, 6

(56) References Cited

U.S. PATENT DOCUMENTS 5,171,853 A 12/1992 Thorp et al. .................. 536/27
5,317,098 A 5/1994 Shizuya et al. ............. 536/231
5,328,824 A 7/1994 Ward et al. .................... 435/6
5,449,767 A 9/1995 Ward et al. .................... 435/6
5,582,829 A * 12/1996 Alliger et al. ........... 424/234.1
5,684,149 A 11/1997 Morrow ...................... 540/474
5,688,670 A * 11/1997 Szostak et al. .......... 435/91.21
5,695,936 A 12/1997 Mandrand et al. ............. 435/6
5,744,308 A * 4/1998 Guillou-Bonnici et al. .... 435/6
5,849,480 A 12/1998 Cros et al. ..................... 435/6
5,871,976 A * 2/1999 Kramer et al. ........... 435/91.51
5,981,734 A * 11/1999 Mirzabekov et al. ...... 536/25.3
5,989,904 A * 11/1999 Das et al. ................ 435/320.1
6,017,707 A 1/2000 Mandrand et al. ............. 435/6

FOREIGN PATENT DOCUMENTS

DE 39 10 151 A1 10/1990
DE 198 15864 A1 10/1999
EP 0 063 879 A2 11/1982
EP 0 097 373 A2 1/1984
EP 0 280 058 A2 8/1988
EP 0 286 898 A2 10/1988
EP 0 302 175 A2 2/1989
EP 0 329 198 A2 8/1989
EP 0 567 841 A2 11/1993
EP 0 801 072 A2 10/1997
FR 2768743 3/1999
FR 2781500 1/2000
WO WO 88/04300 6/1988
WO WO 93/16094 8/1993
WO WO 93/20241 10/1993
WO WO 94/29723 12/1994
WO WO 95/03142 2/1995
WO WO 95/08000 3/1995
WO WO 96/28460 9/1996
WO WO 98/05766 2/1998
WO WO 98/11104 3/1998
WO WO 98/27229 6/1998
WO WO 99/65926 12/1999

OTHER PUBLICATIONS

Zuckermann et al., "Site–specific cleavage of structured RNA by a staphylococcal nuclease–DNA hybrid", Proceedings of the National Academy of Sciences, USA, vol. 86, pp. 1766–1770.*

K. Greisen et al., "PCR Primers and Probes for the 16S rRNA Gene of Most Species of Pathogenic Bacteria, Including Bacteria Found in Cerebrospinal Fluid", *Journal of Clinical Microbiology*, vol. 32, No. 2, Feb. 1994, pp. 335–351.

M. Chee et al., "Accessing Genetic Information with High–Density DNA Arrays", *Science*, 274, Oct. 25, 1996, pp. 610–614.

A. Caviani Pease et al., "Light–Generated Oligonucleotide Arrays for Rapid DNA Sequence Analysis", *Proc. Natl. Acad. Sci. USA*, vol. 91, May 1994, pp. 5022–5026.

J. Chevalier et al., "Biotin and Digoxigenin as Labels for Light and Electron Microscopy in Situ Hybridization Probes: Where Do We Stand?", *The Journal of Histochemistry & Cytochemistry*, vol. 45(4), 1997, pp. 481–491.

R. Breslow et al., "Recognition and Catalysis in Nucleic Acid Chemistry", *Proc. Natl. Acad. Sci. USA*, vol. 90, Feb. 1993, pp. 1201–1207.

AmpliScribe™ T7, T3, and SP6 High Yield Transcription Kits Product Information, Epicentre Technologies, pp. 1–3 (Date Unknown).

A. Troesch et al., "Mycobacterium Species Identification and Rifampin Resistance Testing With High–Density DNA Probe Arrays", *Journal of Clinical Microbiology*, Jan. 1999, pp. 49–55.

T. Furuta et al., "Direct Esterification of Phosphates with Various Halides and its Application to Synthesis of cAMP Alkyl Triesters", *J. Chem. Soc. Perkin Trans.* 1, 1993, pp. 3139–3142.

(List continued on next page.)

*Primary Examiner*—Jeffrey Fredman
*Assistant Examiner*—Arun Kr. Chakrabarti
(74) *Attorney, Agent, or Firm*—Oliff & Berridge, PLC

(57) ABSTRACT

The present invention relates to a process for labeling a synthetic or natural ribonucleic acid (RNA). It also relates to RNA fragments, which have been labeled by fragmenting the RNA to free a terminal phosphate of each fragment for further reaction, and labeling each fragment at the freed terminal phosphate which is located at the 3' end and/or the 5' end of each fragment of the RNA, and to the use of such RNA fragments, for example, in the field of medical diagnosis.

36 Claims, 4 Drawing Sheets

OTHER PUBLICATIONS

Sambrook, Fritsch & Maniatis Document—"Removal of Ethidium Bromide from DNAs Purified by Equilibrium Centrifugation in CsCl–Ethidium Bromide Gradients", *Plasmid Vectors*, Second Edition, 1989, p. 1.46.

M. Mag et al., "Synthesis and Selective Cleavage of an Oligodeoxynucleotide Containing a Bridged Internucleotide 5'phosphorothioate Linkage", *Nucleic Acids Research*, vol. 19, No. 7, pp. 1437–1441, (1991).

C. Tung et al., "Design of Peptide–Acridine Mimics of Ribonuclease Activity", *Proc. Natl. Acad. Sci.*, vol. 89, pp. 7114–7118, (1992).

K. Yoshinari et al., "Oligoamines as Simple and Efficient Catalysts for RNA Hydrolysis", *Journal of American Chemical Society*, vol. 113, pp. 5899–5901, (1991).

A. Modak et al., Toward Chemical Ribonucleases, 2. Synthesis and Characterization of Nucleoside—Bipyridine Conjugates, Hydrolytic Cleavage of RNA by Their Copper(II) Complexes, *Journal of American Chemical Society*, vol. 113, pp. 283–291, (1991).

R. Breslow et al., "Recognition and Catalysis in Nucleic Acid Chemistry", *Proc. Natl. Acad. Sci.*, vol. 90, pp. 1201–1207.

* cited by examiner

5-Bromo-fluorescein

PROCESS FOR LABELING A RIBONUCLEIC ACID, AND LABELED RNA FRAGMENTS WHICH ARE OBTAINED THEREBY

The present invention relates to a novel process for labelling a synthetic or natural ribonucleic acid (RNA).

A synthetic RNA is to be understood as meaning an RNA which is obtained by a technique which was developed by man, for example an amplification technique (PCR followed by a transcription) or a transcriptional amplification technique (TMA). A natural RNA is to be understood as meaning an RNA which is obtained by extraction from a cell, for example a messenger RNA, a ribosomal RNA or a transfer RNA.

The state of the art shows that there are a large number of methods for labelling nucleotides, oligonucleotides or nucleic acids; oligonucleotides and nucleic acids will be referred to by the term polynucleotides. Oligonucleotides can be labelled either during synthesis or by incorporating at least one labelled nucleotide.

A first method consists in attaching the label to the base, whether the latter is a natural base or a modified base. A second method proposes attaching the label to the sugar, again whether the latter be a natural sugar or a modified sugar. A third method relates to attaching the label to the phosphate.

Labelling the base was used, in particular, in the approach of labelling nucleic acids by incorporating directly labelled nucleotides.

Labelling the sugar is often used in the case of nucleic acid probes which are prepared by chemical synthesis.

Labelling the phosphate has also been used for introducing functionlized arms and labels when synthesizing the polynucleotides chemically.

In fact, the skilled person who is to label a nucleotide or a nucleotide analogue or a nucleic acid is inclined to attach the label to the base or to the sugar, which offer him more convenience and more options. This is, furthermore, what emerges from studying a large number of documents such as EP-A-0.329.198, EP-A-0.302.175, EP-A-0.097.373, EP-A-0.063.879, U.S. Pat. No. 5,449,767, U.S. Pat. No. 5,328,824, WO-A-93/16094, DE-A-3.910.151 and EP-A-0.567.841 in the case of the base or EP-A-0.286.898 in the case of the sugar.

Nevertheless, these techniques suffer from a number of drawbacks, the two main ones being the steric hindrance and the effects which are engendered by the presence of a label.

When the base is labelled, the steric hindrance is due to the encroachment of the label on the space where a neighbouring base is present, irrespective of whether this neighbouring base is carried by an adjacent nucleotide of the same strand or by the complementary strand. It is also quite obvious that the presence of the label on the base can impair efficacy and specificity during enzymic incorporation and can have an effect on the quality of the hydrogen bonds between the two complementary strands, something which can be injurious to hybridization.

When the sugar is labelled, the steric hindrance is due to the encroachment of the label on the space where an adjacent sugar carried by the same strand is present. This presence of the label can move apart two adjacent bases which are carried by the same strand and, as a consequence, prevent satisfactory hybridization with the complementary strand due to the fact that the hydrogen bonds between the strands are not optimal.

The technique of attaching the label to the phosphate is more complex than the technique involved in functionalizing the base or the sugar.

Even so, some documents have proposed techniques for labelling the phosphate. This applies, for example, to document EP-A-0.280.058, which describes labelling a nucleotide by attaching the label to the phosphate, with the latter being attached to the sugar in the 2' and/or 5' positions, when the nucleotide is a deoxyribonucleotide, and in the 2', 3' and/or 5' positions when the nucleotide is a ribonucleotide. This document also describes a polynucleotide or oligonucleotide which comprises at least one labelled nucleotide as described above; this nucleotide is incorporated into the polynucleotide or oligonucleotide during synthesis.

However, the labelling which is proposed by document EP-A-0.280.058 does not enable the nucleic acids to be labelled uniformly. This is because the incorporation of the labelled nucleotides into the polynucleotides cannot be controlled; it depends entirely on the composition of polynucleotides which is to be synthesized. Thus, some polynucleotides may contain a large number of labelled nucleotides whereas others may not contain any at all. As a result, the intensity of the signal emitted by these nucleic acids will not be uniform, something which could easily make it difficult to interpret the results when detecting the nucleic acids.

In this case, the labelling is incorporated biologically without there being any control of the positions of the labelled nucleotides.

The document U.S. Pat. No. 5,317,098 relates to nucleic acids which are labelled at their 5' ends. This attachment uses imidazole and a linker arm. There is no associated fragmentation. Furthermore, phosphate is added; kinase is therefore used.

Nevertheless, a phosphate will logically be present at each free end of the nucleic acid, leading to at least one additional step. This labelling is not associated with any fragmentation.

In addition, the labelling described by the preceding two documents is carried out on large nucleic acids. Thus, no fragmentation stage, also termed a cleavage stage, wets described before the labelling steps. As a result, the duplexes formed after hybridization are not stable when these target nucleic acids are hybridized to capture probes. This also applies when the polynucleotides are used as detection probes. The reasons may be due to steric hindrance or to a lack of specificity between the polynucleotide, which has been synthesized, and its target, which is not necessarily of the same size. This will therefore result in a quantitative and qualitative loss of the signal.

Steric hindrance may not only be the result of the length of the nucleic acid but also of the existence or the conservation of secondary structures. Fragmentation makes it possible to destroy these structures and in this way to optimize hybridization. This steric hindrance plays a particularly important role in the case of hybridization to surfaces which contain a high density of capture probes, for example the DNA chips developed by the company Affymetrix ("Accessing Genetic Information with High-Density DNA arrays", M. Shee et al., Science, 274, 610–614. "Light-generated oligonucleotide arrays for rapid DNA sequence analysis", A. Caviani Pease et al., Proc. Natl. Acad. Sci. USA, 1994, 91, 5022–5026). In this technology, the capture probes are generally of reduced size, being of about twenty nucleotides.

A large number of methods are described in the state of the art for fragmenting nucleic acids.

In the first place, the fragmentation can be enzymic, i.e. the nucleic acids can be fragmented by nucleases (DNases or RNases). This generates small fragments having 3'-OH, 5'-OH, 3'-phosphate and 5'-phosphate ends.

In the second place, the fragmentation can be chemical. For example, in the case of DNAs, it is possible to depurinate or depyrimidinate the DNAs, which are then fragmented in the presence of a base by a mechanism termed "β-elimination". The DNAs can be fragmented by oxidation, alkylation or free radical addition mechanisms, inter alia. Metal cations, which are often combined with organic molecules used as chemical catalysts, for example imidazole, are used for fragmenting RNAs. This fragmentation is preferably carried out in an alkaline medium and generates fragments having 3'-phosphate ends.

However, the objective of these fragmentations is not that of facilitating or permitting labelling.

Document WO-A-88/04300 proposes a method for fragmenting and labelling RNA, with the fragmentation being carried out using RNA which possesses enzymic properties, i.e. ribozymes. With each cleavage, this fragmentation by ribozymes releases a nucleic acid (5') HO end and a nucleic acid (3') HO—$PO_2$ end. The labelling, which is solely radioactive labelling, is then effected using an incorporation enzyme (kinase), which incorporates an added radioactive phosphate which is derived from a molecule of γ-GTP. This attachment is effected solely at the 5' end. Furthermore, the fragmentation is only carried out by ribozymes, implying the existence of a specificity between the ribozymes and the target nucleic acids to be cleaved. The phosphate then acts as the label.

Our invention attaches a label to the only phosphate of a nucleic acid fragment which is released during the cleavage. There is no specificity that any type of nucleic acid can be fragmented in a random manner. Thus, our process makes it possible to prepare detection probes, for example. Finally, the phosphate is only a linker arm between the nucleic acid and the label.

No process of fragmenting before labelling in one or two steps has been described in the prior art.

The present invention therefore proposes a process which overcomes the previously mentioned drawbacks. Thus, this process makes it possible to obtain RNA fragments which are uniformly labelled once the fragmentation has been completed. In addition, the fragmentation makes it possible to obtain fragments which are of an optimum size for a possible hybridization. With the quality of the hybridization having been improved, the detection of this hybridization will be more rapid and efficient.

Labelling is understood as being the attachment of a label which is able to generate a detectable signal either directly or indirectly. The following is a non-limiting list of these labels:

- enzymes which produce a detectable signal, for example by colorimetry, fluorescence, luminescence, such as horseradish peroxidase, alkaline phosphatase, β-galactosidase and glucose-6-phosphate dehydrogenase,
- chromophores, such as fluorescent and luminescent compounds and dyes,
- groups having an electron density which can be detected by electron microscopy or by their electrical properties such as conductivity, amperometry, voltametry and impedance,
- detectable groups, for example whose molecules are of sizes which are sufficient to induce detectable modifications in their physical and/or chemical characteristics; this detection can be effected by means of optical methods such as diffraction, surface plasmon resonance, surface variation and angle of contact variation, or physical methods such as atomic force spectroscopy and the tunnel effect,
- radioactive molecules such as $^{32}P$, $^{35}S$ or $^{125}I$.

Indirect systems can also be used, such as ligands which are able to react with an anti-ligand. Ligands/anti-ligand pairs are well known to the skilled person, as, for example, in the case of the following pairs; biotin/streptavidin, hapten/antibody, antigen/antibody, peptide/antibody, sugar/lectin and polynucleotide/complementary polynucleotide. In this case, it is the ligand which carries the binding agent. The anti-ligand can be detected directly by means of the labels described in the preceding paragraph or be itself detectable by means of a ligand/anti-ligand.

To this end, the present invention relates to a process for labelling a synthetic or natural ribonucleic acid (RNA), characterized in that it consists:

- in fragmenting the RNA, and
- in labelling at the level of the terminal phosphate which is located at the 3' end and/or the 5 ' end of each fragment of the said RNA, the said terminal phosphate having been freed during the fragmentation.

According to a preferred mode of operation, the labelling of tile 3' end of each fragment of the RNA is effected in the case of each fragment apart from the fragment which constitutes the 3' and/or 5' end of the starting RNA, and/or the labelling of the 5' end of each fragment of the RNA is effected in the case of each fragment apart from the fragment which constitutes the 5' end of the starting RNA.

According to a first embodiment, the fragmentation and the labelling are effected in one step.

According to a second embodiment, the fragmentation and the labelling are effected in two steps.

Whatever the embodiment, labelling of the 3' end or the 5' end of an RNA fragment is effected by binding a reactive function which is carried by a label, or which is capable of being subsequently linked to at least one label, to the phosphate which is in the 2' position, in the 3' position or in the cyclic monophosphate 2'–3' position, with respect to the ribose. When there are at least two labels, the technique is then a signal-amplification technique.

The fragmentation and/or the labelling of the 3' end or the 5' end of an RNA fragment is effected by binding a nucleophilic, electrophilic or halide function which is carried by a label, or which is capable of being subsequently linked to a label, to the phosphate in the 2' position, in the 3' position or in the cyclic monophosphate 2'–3' position, with respect to the ribose.

The fragmentation of the RNA is effected enzymically, chemically or physically.

The enzymic fragmentation of the RNA is carried out by means of nucleases.

The chemical fragmentation of the RNA is carried out by means of metal cations which may or may not be combined with a chemical catalyst.

In this case, the metal cations are $Mg^{++}$, $Mn^{++}$, $Cu^{++}$, $Co^{++}$and/or $Zn^{++}$ions and the chemical catalyst consists of imidazole, a substituted analogue, for example N-methylimidazole, or any chemical molecule which has an affinity for the RNA and which carries an imidazole nucleus or a substituted analogue.

The physical fragmentation of the RNA is carried out by means of sonication or by means of radiation.

In all the cases in point, the labelling of the 3' end or the 5' end of an RNA fragment is effected by binding a molecule R—X, where R consists of the label and X is the agent for binding the label to the RNA, such as a hydroxyl, amine, hydrazine, alkoxylamine, alkyl halide, phenylmethyl halide, iodoacetamide or maleimide grouping, to the phosphate which is linked to the 2' position, to the 3' position or to the cyclic monophosphate 2'–3' position of the ribose.

The present invention also consists of an RNA fragment which is obtained by the process, in accordance with the features expounded above, which is characterized in that the RNA fragment comprises, on the one hand, a single nucleotide which is labelled at the level of the terminal phosphate which is located at the 3' end or the 5' end of the RNA fragment, the said terminal phosphate having been freed during the fragmentation, and, on the other hand, at least one other nucleotide whose base (purine: adenine/guanine or pyrimidine: uracyl/cytosine) is identical to that of the labelled nucleotide.

This RNA fragment comprises from 10 to 100 nucleotides, preferably from 30 to 70 nucleotides and preferably from 40 to 60 nucleotides.

According to a preferred embodiment, the RNA fragment comprises at least one thiophosphate nucleotide.

In addition, the labelled nucleotide is a thiophosphate nucleotide.

The invention relates to the use of an RNA fragment, as defined above, as a probe for detecting an RNA and/or a DNA or an RNA fragment and/or a DNA fragment.

The invention finally relates to the use of an RNA fragment, as defined above, as a labelled target which is able to bind to a capture probe.

The attached figures show different ways of synthesizing RNA fragments which are labelled in accordance with the invention, as well as the fragments which are obtained thereby. They represent particular embodiments and cannot be regarded as limiting the scope of the present invention.

Figure 6:
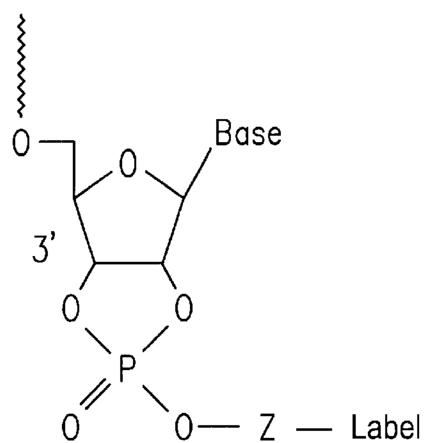

FIG. 6 shows a diagram of the 3' end of an RNA fragment which has been obtained by a process according to the invention, where the label is attached to a natural phosphate, with Z being a coupling arm, also termed a spacer arm, as defined in one of the applicant's previous patent applications which was filed on Aug. 1, 1997 under the number PCT/FR97/01445. This definition of Z also applies for FIGS. 7 and 8.

Figure 7:
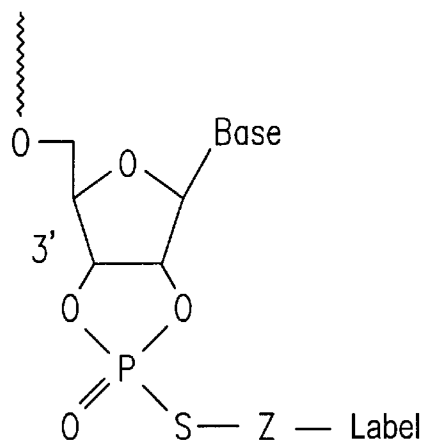

FIG. 7 shows a diagram of the 3' end of an RNA fragment which was obtained by a process according to the present invention, where the label is bound to a thiophosphate.

Figure 8:
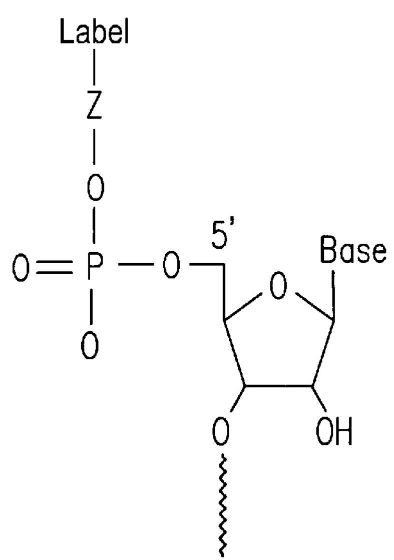

Finally, FIG. 8 shows a diagram of the 5' end of an RNA fragment which was obtained by a process according to the present invention, where the label is attached to a natural phosphate.

Figure 2:
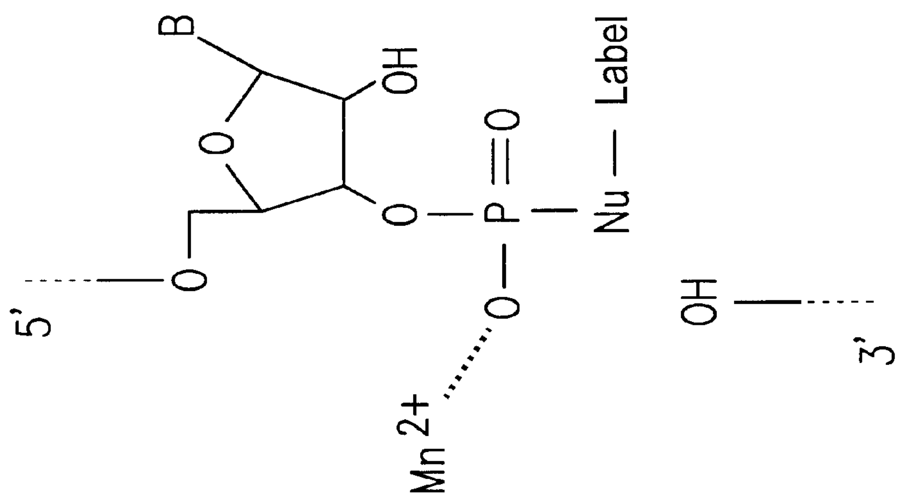
FIG. 2 shows a diagram of the fragmentation and labelling of an RNA with a label which carries a nucleophilic function.
Figure 2:
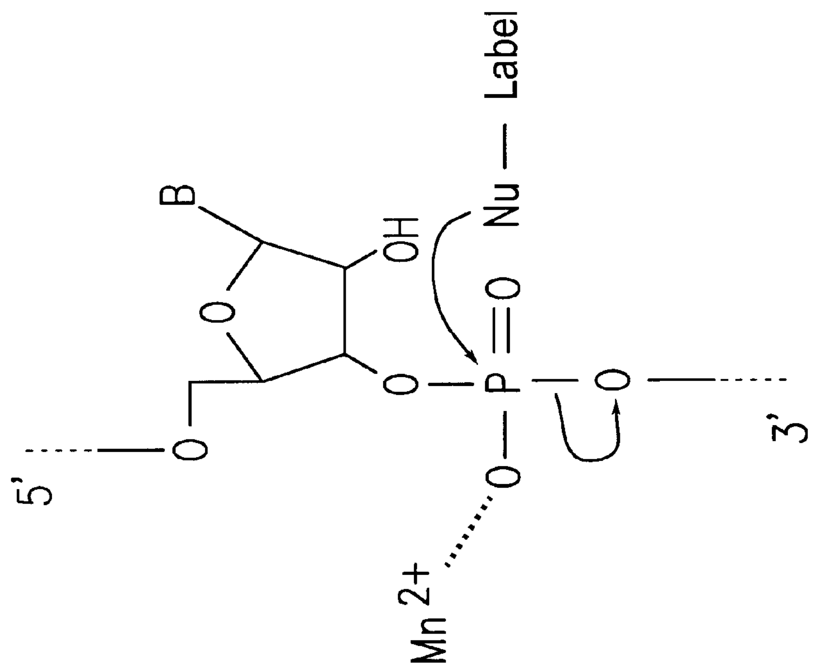

The process described in the figures can be a one-step process, as is the case in FIG. 2, where the fragmentation and the labelling are carried out jointly using a labelled nucleophile.

Figure 1:
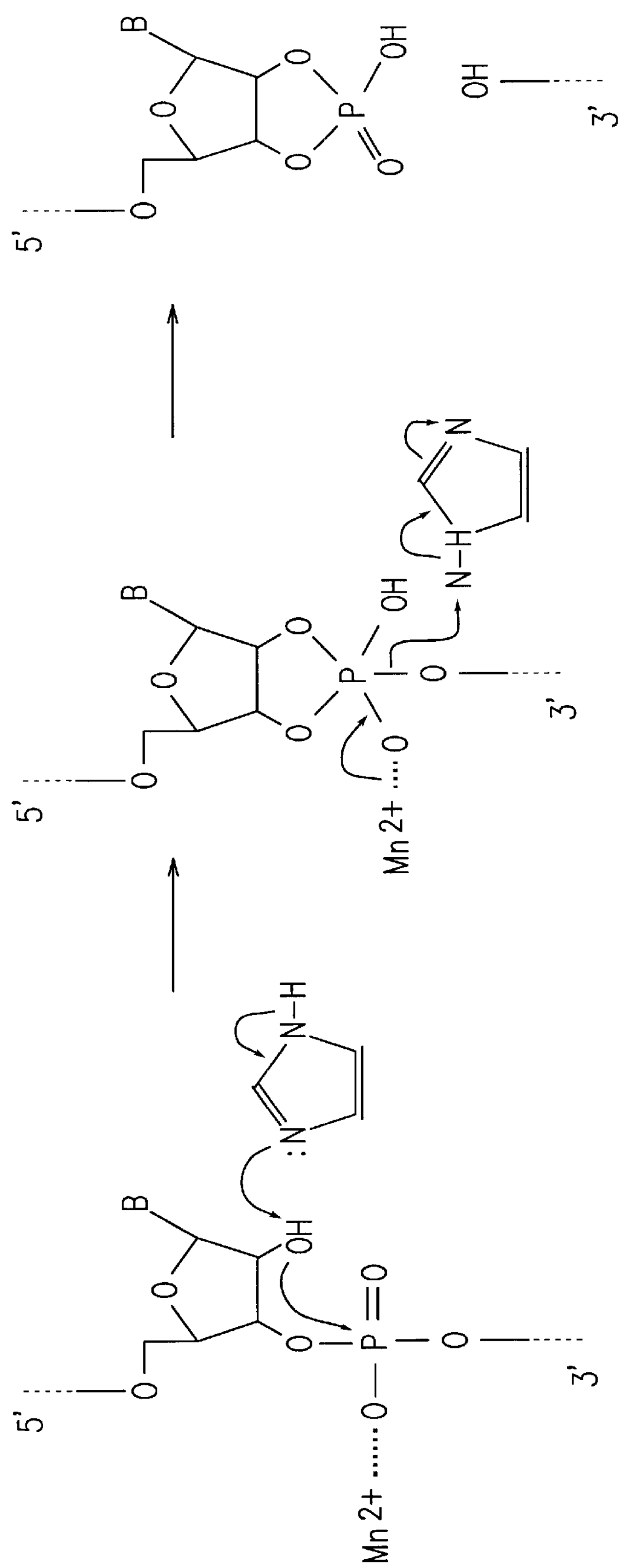
FIG. 1 shows a diagram of the chemical fragmentation of an RNA in the presence of $Mn^{++}$cations and imidazole.

The process can also be carried out in two steps. The first step is a fragmentation step as shown in FIG. 1, resulting from the action of imidazole, for example. The second and final step is one of labelling using a label as shown in a non-limiting manner in FIGS. 3 to 5; this labelling is effected on the freed phosphate and is shown in FIGS. 6 to 8.

EXAMPLE 1

Preparing RNA Amplicons and RNA Transcripts

A—Preparing Natural Amplicons

The natural amplicons (single-stranded RNA) are prepared using the TMA (Transcription-Mediated Amplification) amplification technique developed by Gen Probe (San Diego, Calif.). The RNA strand which is amplified corresponds to the 16S sequence of the *Mycobacterium tuberculosis* (ATCC -27294) ribosomes. The 16 S RNA was cloned into a plasmid and this plasmid was then transformed into bacteria obtained from the TA Cloning Dual Promoter kit (Ref.: K2050-01-Invitrogen, Groningen, The Netherlands). After culturing in LB medium (described, for example, in Maniatis), and extracting the bacterial DNA by alkaline lysis, the strand was transcribed using the "Ampli Scribe T7 Transcription" kit (Ref.: AS 2607—Epicentre Technologies (Madison, Wis.). The number of copies per microliter was determined by measuring the absorbance at 260 nm.

B—Preparing RNA Transcripts from DNA which has Been Obtained by TMA

It is first of all appropriate to note that the TMA amplification product contains DNA amplicons in addition to RNA amplicons in a proportion of approximately 90% RNA to 10% DNA. These DNA amplicons were used to produce single-stranded DNAs by means of in-vitro transcription.

Amplicons were first of all obtained, in a first step, using the Mycobacterium Tuberculosis Direct (MTD) kit from Gen Probe (Ref.: 1001E) in the same manner as before using the protocol described in step 1-A above.

In a second step, the transcription was carried out on a DNA template obtained by the TMA of the first step, using a *Mycobacterium tuberculosis* 16S RNA template.

The transcription was carried out starting from 5 $\mu$l of TMA products and using the MEGAscript T7 kit (AMBION, Austin, Tex., Ref.: 1334). The reaction was carried out at 37° C. for one hour.

C—Preparing RNA Transcripts from the DNA which was Obtained by PCR

Using a spatula, one or two colonies (3–5 mm in diameter, equivalent to $10^8$ bacteria) were collected from a bacterial isolate (ATCC-27294), which was cultured on Lowenstein-Jensen medium, and resuspended in 250 $\mu$l of sterile water in a 1.5 ml Eppendorf tube. The nucleic acids were extracted from the cell material of the bacterial suspension by means of vigorous shaking using a vortex in the presence of glass beads. Such an extraction is well described in patent applications FR97/12164, dated Sep. 23, 1997, and FR98/09583, dated Jul. 23, 1998, which have been filed by the applicant.

An aliquot of 5 $\mu$l of the lysate was added directly to the PCR reaction. It is also possible to add 20 ng of plasmid DNA directly to the PCR reaction.

The hypervariable 16S region was amplified by PCR using primers which were specific for the Mycobacterium genus (positions 213–236 and 394–415 on the *M. tuberculosis* reference sequence, M20940, Genbank), with the size of the amplicon being 202 base pairs (bp). The primers also contain bacteriophage T3 or T7 promoter sequences at their 5' end.

The PCR was carried out in a 100 $\mu$l reaction volume containing 50 mM KCl, 10 mM Tris, pH=8.3, 1.5 mM $MgCl_2$, 0.001% (m/v) gelatin, 5% (v/v) DMSO, 0.5 $\mu$M of each primer, 200 $\mu$M of each of the four deoxynucleotide triphosphates and 1.5 units of Taq polymerase (AmpliTaq, Perkin-Elmer, Norwalk, Conn.). The PCR reaction was carried out in a Perkin-Elmer 2400 thermocycler (Norwalk, Conn.) using an initial denaturation step at 94° C. for 5 minutes (min), and 35 cycles of 45 seconds (s) at 94° C., 30 s at 60° C. and 30 s at 72° C., followed by 10 min at 72° C. after the last cycle. The PCR reaction products were analysed by agarose gel electrophoresis.

The amplicons containing the promoters were used to produce single-stranded RNA by means of in-vitro transcription. Each reaction, which is of 20 μl volume, contains approximately 50 ng of PCR products, 20 units of T3 or T7 polymerase (Promega, Madison, Wis.), 40 mM Tris-acetate buffer, pH=8.1, 100 mM magnesium acetate [$Mg(AcO)_2$], 10 mM DTT and 1.25 mM of each nucleotide triphosphate (ATP, CTP, GTP and UTB). The reaction was carried out at 37° C. for one hour.

D—Preparing RNA Transcripts Containing Thiophosphates from the DNA Obtained by PCR:

The amplicons obtained by PCR, in accordance with the preceding step 1-C, and containing the promoters, were used to produce single-stranded RNA containing thiophosphates by mean of in-vitro transcription. In each reaction, which is of 20 μl volume, then containing approximately 50 ng of PCR products, 20 units of T3 or T7 polymerase (Promega, Madison, Wis.), 40 mM Tris-acetate buffer, pH=8.1, 100 mM magnesium acetate [$Mg(AcO)_2$], 10 mM DTT and 1.25 mM of each sort of nucleotide trisphosphate or thiophosphate (ATP-α-thiophosphate (ATP-α-S) or CTP-α-thiophosphate (CTP-α-S)), using two different solutions:

ATP-α-S, CTP, GTP and UTP, or

ATP, CTP-α-S, GTP and UTP

The reaction took place at 37° C. for one hour.

The thiophosphate nucleotide which was used was present at 100% of the 1.25 mM, therefore substituting for the corresponding natural nucleotide. In each case, the transcription product was analysed by electrophoresis on a 6% polyacrylamide gel in the presence of 7M urea. After staining the ethiduim bromide, the size of the transcript is checked and quantified by comparison with a standard which was loaded onto the gel.

The nucleotides ATP-α-S and CTP-α-S were obtained from N&N Life Science Products (Boston, Mass. USA) .

EXAMPLE 2

Chemical Fragmentation of the RNA

Chemical fragmentation of RNA is often catalyzed by metal cations ($Mn^{++}$, $Mg^{++}$, etc.) which, by binding to the phosphate group, neutralize the negative charge of the oxygen and thus facilitate nucleophilic attack by the hydroxyl on the phosphate in the 2' position of the ribose.

This nucleophilic attack can be reinforced by the presence of molecules which are proton donors and acceptors, such as the imidazole nucleus (R. Breslow and R. Xu, Proc. Natl. Acad. Sci. USA, 90, 1201–1207, 1993), as is indeed depicted in FIG. 1.

The fragmentation can be carried out at different temperatures and under different conditions. Two different types of fragmentations were carried out, as described below.

There can be a fragmentation at 60° C. In this case, the *Mycobacterium tuberculosis* 16S RNA transcripts, termed Mycobacterial transcripts below, which comprise 330 nucleotides (approximately 66 pmol), are incubated in an aqueous solution of imidazole (30 mM) and manganese chloride (30 mM) at 60° C. for 30 min. The total volume of the fragmentation solution is 100 μl. The fragmented RNA is then analysed on a polyacrylamide gel (6X, 7 M urea), and stained with ethidium bromide.

There can also be a fragmentation at 95° C. In that case, the Mycobacterial 330 nucleotide (66 pmol) 16S RNA transcripts are incubated in an aqueous solution of magnesium chloride (30 mM) at 95° C. for 30 min. The total volume of the fragmentation solution is 100 μl. The fragmented RNA is then analysed on a polyacrylamide gel (6X, 7 M urea), and stained with ethidium bromide.

In the two types of fragmentation, the gel analysis shows the disappearance of the starting compound and the appearance of several shorter fragments, the most significant population of which has a size of between 20 and 50 nucleotides.

These are the two protocols which were used for introducing a fluorescent label onto the RNA chain during its fragmentation.

EXAMPLE 3

Labelling During Fragmentation by Introducing Labels Carrying a Nucleophilic Function A function which is more nucleophilic than the hydroxyl in the 2' position of the ribose can attack the neutralized phosphate and thus fragment the RNA chain by generating fragments which are linked to this function via the phosphate group. As shown in FIG. 2, this function can be linked to a label in order to generate labelled RNA fragments.

Figure 4:
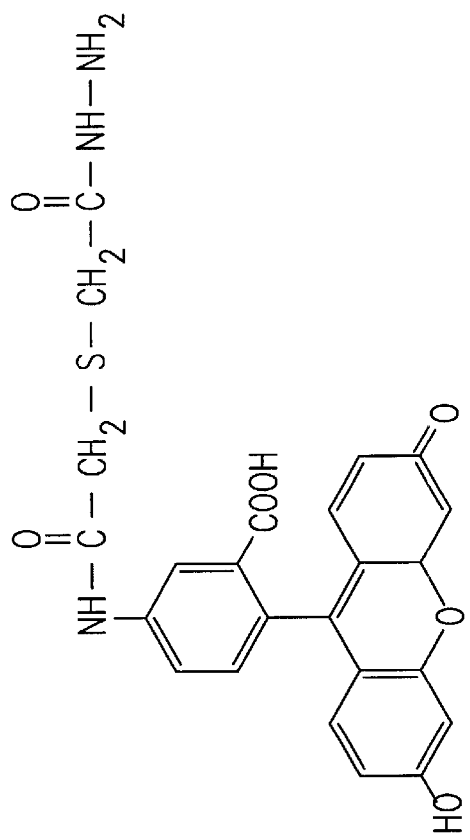
FIG. 4 shows a label which can be used together with the process shown in FIG. 2, with this label consisting of fluorescein-hydrazide.
Figure 3:
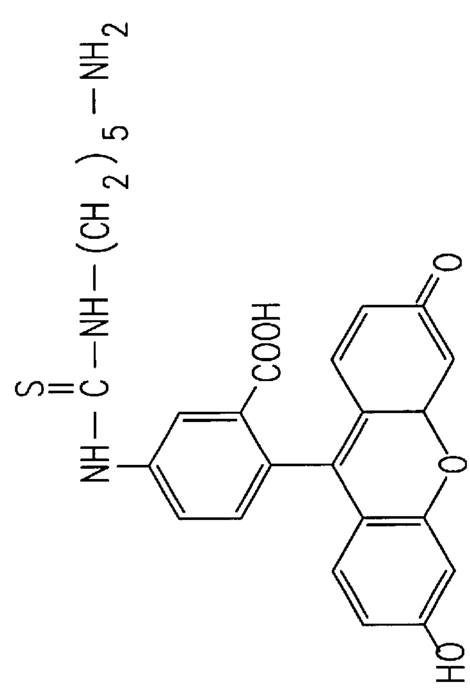
FIG. 3 shows a label which can be used together with the process shown in FIG. 2, with this label consisting of fluorescein-cadaverine.

Fluoroscein-cadaverine, which is shown in FIG. 3 and which carries an amine function, and fluorescein-hydrazide, which is detailed in FIG. 4 and which carries a hydrazide function, were used for labelling a Mycobacterial (330 nucleotide) 16S RNA during the fragmentation at 65° C. This RNA was obtained as described in Example 1B.

The fluorescein-cadaverine and the fluorescein-hydrazide were dissolved in DMF to a final concentration of 7.5 mM. They were obtained from Molecular Probes (Eugene, Oreg., USA).

1 μl of the label solution (7.5 mM in DMF) was added to the target 16S RNA (66 pmol) , which was in solution in the 65° C. fragmentation buffer (Example 1). After incubating at 65° C. for 30 minutes, each reaction product was hybridized, detected and analysed on a DNA chip (Affymetrix, Santa Clara, Calif. USA) in accordance with the protocol supplied by the manufacturer. These chips are designed to identify a particular region, in the present case the 213–415 region of the “Genbank” M20940 sequence of the *Mycobacterium tuberculosis* 16S RNA. When using the fluorescein-cadaverine or the fluorescein-hydrazide, 66% of the sequence was found. This indicates that the label was in each case introduced during the fragmentation, thereby generating fluorescent and detectable fragments. A good description of such an identification is given in the article by A. Troesch et al., J. Clin. Microbiol. 37(1), pp. 49–55, 1999.

EXAMPLE 4

Figure 5:
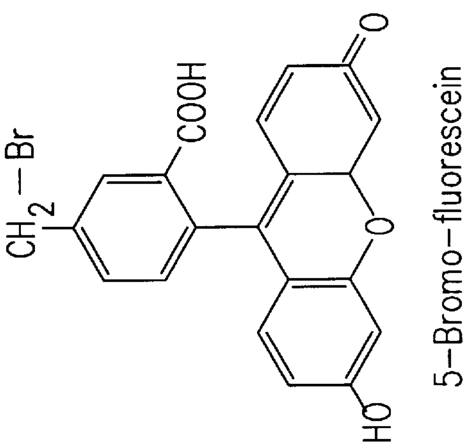
FIG. 5 shows a halogenated label which can be used together with the process according to the invention.

Labelling During Fragmentation by Way of a Label Which Carries a Methyl Halide It is known that a monophosphate can be substituted by a label carrying a phenylmethyl halide grouping (see T. Furuta et al., J. Chem. Soc. Perkin Trans. 1 3139–3142, 1993). 5-Bromofluoroscein, which is shown in FIG. 5, belongs to this category of halogenated labels.

Since it is known that the fragmentation reaction frees cyclic monophosphate 3' ends in equilibrium with the open forms, the fragmentation step can be used to attach a label to the 3' phosphate groupings of the RNA fragments.

A—Labelling RNA Amplicons Obtained by TMA Amplification

Mycobacterial (330 nucleotide) 16S RNA amplicons were prepared by TMA amplification as described in Example 1-A. 5-Bromofluoroscein was obtained from Molecular Probes (Eugene, Oreg., USA). Manganese chloride was obtained from Sigma and imidazole was obtained from Aldrich.

A-I. Labelling 50 μl of TMA: Protocol Using 6 mM Imidazole and 60 mM Manganese Chloride 15 μl of a solution of imidazole (0.1 M), 15 μl of a solution of manganese chloride (1 M), 2.5 μl of 5-bromofluorescein (100 mM) in DMSO, and then 50 μl of TMA products, were added to 165 μl of RNase-free water (Sigma) in a 5 ml polypropylene tube whose diameter and length dimensions are 12 mm and 75 mm, respectively. The mixture is homogenized by shaking on a vortex and incubated at 60° C. for 30 min.

After incubation, the solution was used, without any purification, for hybridization to, and detection on, DNA chips (Affymetrix, Santa Clara, Calif. USA), also termed biochips. The protocol used for this hybridization step is that supplied by the manufacturer. These Chips are designed for identifying the 213–415 region of the "Genbank" M20940 sequence of *Mycobacterium tuberculosis* 16S RNA. The results are given in Table 1 below:

TABLE 1

Results of labelling RNA fragments which were labelled without purification

| Score obtained | Median intensity (Rfu) | Background (Rfu) |
|---|---|---|
| 91.2% | 1727 | 834 |

In the identification by means of biochip technology, the percentage identification or score obtained corresponds to a percentage analysis with respect to the reference sequence. 91.2% of the sequence is identified and the median intensity is 1727 Rfu. This indicates that, in each case, the label was introduced during the fragmentation, thereby generating fluorescent and detectable fragments. It is also important to note that the labelling reaction product was hybridized directly to the chip without any prior purification. This result is very interesting and shows that unpurified RNA transcripts can be efficiently labelled by means of this fragmentation protocol using imidazole and manganese chloride.

We subsequently attempted to label 50 μl and then 100 μl (total volume) of a TMA reaction described in Example 1-A using the above-described labelling protocol and a purification step before hybridization to the DNA chip.

Following incubation at 65° C., the two labelling reaction products contain 50 μl and 100 μl of TMA were treated with 1-butanol in order to extract the excess of 5-bromofluorescein This extraction was carried out twice using 1 ml of water-saturated 1-butanol on each occasion. This extraction, like those which follow, is well known in the state of the art. Supplementary information can, in particular, be found in the document Sambrook, Fritsch & Maniatis, Molecular Cloning (Second Edition, 1.46) Cold Spring Harbor Laboratory Press, 1989. The results are given in Table 2 below. These measurements are made after hybridizing to the biochip and reading the result.

TABLE 2

Results of labelling RNA fragments which were labelled with purification

| Volume of TMA | Score obtained | Median intensity (Rfu) | Background (Rfu) |
|---|---|---|---|
| 50 μl | 95.9% | 6867 | 169 |
| 100 μl | 96.7% | 5775 | 275 |

The percentage identification or score obtained is in the neighbourhood of 100%, and the intensities obtained are very high. This shows that a purification step before hybridization can improve the identification percentages and the labelling intensities and reduce the background. It is clear that any additional post-hybridization washing cycles are no longer necessary.

A—2. Labelling 50 μl of TMA: Protocol Using 30 mM Imidazole and 30 mM Manganese Chloride 75 μl of a solution of imidazole (0.1 M), 7.5 μl of a solution of manganese chloride (1 M), 2.5 μl of 5-bromofluorescein (100 mM) in DMSO, and then 50 μl of TMA products, are added to 112 μl of RNase-free water (Sigma) in a 5 ml polypropylene tube. The mixture is homogenized by shaking on a vortex and incubated at 60° C. for 30 min.

Following incubation, the two labelling reaction products obtained from 50 μl of TMA products were treated with 1-butanol in order to extract the excess of 5-bromofluoroescein. This extraction was carried out twice using 1 ml of water-saturated 1-butanol on each occasion. The results are given in Table 3 below. These measurements are made after hybridization to the biochip and reading the results.

TABLE 3

Results of labelling RNA fragments which were labelled with purification

| Volume of TMA | Score obtained | Median intensity (Rfu) | Background (Rfu) |
|---|---|---|---|
| 50 μl | 92.7% | 444 | 131 |

92.7% of the amplified sequence is identified and the median intensity is 444 Rfu. These results show that the protocol using 30 mM imidazole and 30 mM $MnCl_2$ produces labelled amplicon fragments. However, the intensity level is lower than that obtained with the imidazole/$MnCl_2$=6 mM/60 mM protocol.

This strategy can be optimized. The high concentration of metal salt is certainly very important for the labelling reaction. Other metals or other buffers can be used for carrying out this labelling reaction during the fragmentation.

B—Labelling RNA Transcripts Obtained by Post-TMA Amplification Transcription

Target mycobacterial (330 nucleotide) 16S RNA transcripts were prepared by transcription as described in Example 1-B.

15 μl of a solution of imidazole (0.1 M), 15 μl of a solution of manganese chloride (1 M) , 2.5 μl of 5-bromofluoroscein (100 mM) in DMSO, and then 50 μl of transcription product, are added to 165 μl of RNase-free water (Sigma) in a 5 ml polypropylene tube. The mixture is homogenized by shaking on a vortex and incubated at 60° C. for 30 min.

Following incubation, the solution was treated as described in Example 3 (A-1) in order to remove the excess of 5-bromofluorescein. The labelled fragments was then hybridized to, and detected on, the DNA chip (Affymetrix, Santa Clara, Calif. USA) designed for identifying the 213–415 region of the "Genbank" M20940 sequence of the *Mycobacterium tuberculosis* 16S RNA. The results are given in Table 4 below.

TABLE 4

Results of labelling RNA obtained by post-TMA amplification transcription

| Score obtained | Median intensity (Rfu) | Background (Rfu) |
|---|---|---|
| 97.6% | 1426 | 147 |

97.6% of the sequence is identified and the median intensity is 1426 Rfu. This results shows that the labelling-during-fragmentation strategy used for labelling the RNA produced by post-TMA transcription is effective. These target RNA, transcripts are used in the labelling reaction without any purification.

C—Labelling post-PCR Amplification RNA Transcripts Containing Thiophosphates

Target mycobacterial (330 nucleotide) 16S RNA samples were produced by means of post-PCR transcription reactions in which 100% of the adenosine triphosphate (ATP) was replaced with ATP-α-thio (two experiments were carried out) or else 100% of the cytidine triphosphate (CTP) was replaced with CTP-α-thio (one experiment was carried out), as shown in Example 1-D.

These RNA samples were labelled, using the above-described protocol, in the presence of imidazole and manganese chloride. After having been incubated at 65° C. for 30 min, the reaction product was hybridized to, and detected and analysed on a DNA chip (Affymetrix, Santa Clara, Calif. USA) in accordance with the protocol supplied by the manufacturer. The results are given in Table 5 below.

TABLE 5

Results of labelling RNA samples which contain thiophosphates and which were obtained by post-PCR amplification transcription

| Transcripts | Score obtained | Median intensity (Rfu) |
|---|---|---|
| ATP-α-S | 97.1% | 1186 |
| | 100% | 1290 |
| CTP-α-S | 93.6% | 1027 |

97.1 and 100% of the sequences are identified in the case of the ATP-α-S and 93.6% of the sequence is identified in the case of the CTP-α-S. The median intensities are between 1000 and 1300 Rfu. This result shows that the labelling-during-fragmentation strategy used for labelling the thiophosphate-containing RNA samples is effective and even as effective as in the case of nucleotides which do not contain any sulphur. These target RNA transcripts are used in the labelling reaction without any purification.

EXAMPLE 5

Labelling Natural RNA

A bacterial suspension is obtained from a pure strain which has been isolated on solid medium. This suspension, which is prepared in sterile water, is standardized to a McFarland index of 2 (that is approximately $3.10^6$ bacteria/ml) and then centrifuged in an Eppendorf tube for 1 min.

The RNA is extracted from the bacterial biomass in the following manner. The bacterial pellet lysed by resuspending it in 100 μl of lysis buffer (30 mM Tris-HCl, 5 mM EDTA, 100 mM NaCl, 2% SDS, 5 mg of proteinase K/ml, pH 7.3, in the presence of 50 μl of 100 μm-diameter round glass beads manufactured by VIAl, France). The mixture is vortexed for 30 sec. It is then incubated at 37° C. for 15 min. 100 μl of saturated phenol are then added. This mixture is vortexed for 30 sec. The aqueous phase is recovered and then extracted with 100 μl of chloroform. This mixture is then once again vortexed for 30 sec. The aqueous phase is recovered once again. Two ether extractions are carried out and this solvent is evaporated. There then remains approximately 50 μl of aqueous phase containing the total RNA. The Qiagen RNeasy kit can alternatively be used for this extraction.

The technique described in the present invention is used in the following manner to label the total RNA from the bacterial biomass by adding the reagents in the following order:

extracted total RNA (50 μl), water (qs for 100 μl),

6 μl of 1 M imidazole (60 mM final concentration),

6 μl of 1 M $MnCl_2$ (60 mM final concentration), the solution is vortexed for 10 sec, 2 μl of 50 mM 5-bromofluoroscein (1 mM final concentration), the mixture is homogenized by drawing it up several times using a pipette, the mixture is vortexed once again for 1 sec, the mixture is centrifuged for 1 sec in order to collect at the bottom of the tube, and the tube is incubated at 60° C. for 30 min.

The following procedure is then adopted for removing excess free label. The following are added to 100 μl of labelled mixture:

40 μl of salmon sperm DNA

100 μl of 3 M sodium acetate (610 mM final concentration), pH 5.2

250 μl of cold isopropanol (−20° C.)

The mixture is vortexed and then centrifuged for 1 min. The supernatant is discarded. The pellet is then resuspended in hybridization buffer (6×SSPE, 5 mM DTAB, 3 M betaine, 0.05% Triton, 250 μg of herring sperm DNA/ml).

Ethidium bromide is used to visualize the following samples on a 1% agarose gel:

an aliquot of the total RNA preparation before labelling in accordance with the invention (A), an aliquot of the total RNA preparation after labelling in accordance with the invention (B).

The following is noted after visualizing the ethidium bromide under ultraviolet (UV) light:

in the case of the A well, the presence of bands characteristic of the major RNA species, with, from the top downwards: 23S, 16S and then a diffuse band corresponding to the messenger RNA population, in the case of the B well, the presence at the bottom of the gel of a population corresponding to the total fragmented RNA mixture.

The following is noted after visualizing the fluoroscein:

in the case of the A well: nothing at all, in the case of the B well, the presence at the bottom of the gel of a population which corresponds to the fragmented RNA mixture and which is labelled covalently with fluoroscein, demonstrating that the RNA samples were fragmented and labelled. This control was carried out for all the bacterial species described in the table below.

An aliquot of the RNA which was labelled in this way is hybridized to a glass solid support (biochip) to which oligonucleotides have been grafted by photolithography; these oligonucleotides enable the different species to be identified by a method equivalent to that described in the article by A. Troesch et al., J. Clin Microbiol., 37(1), pp. 49–55, 1999. The results are shown in Table 6 below.

TABLE 6

Results of labelling natural RNA samples from different species

| Species | International strain reference | Internal strain reference | Score obtained |
|---|---|---|---|
| *Escherichia coli* | ATCC11775T | 7308009 | 86.3% |
| *Streptococcus pneumoniae* | NCTC7465T | 7804060 | 87.2% |
| *Klebsiella pneumoniae* | ATCC13883T | 7308012 | 84.6% |
| *Pseudonomonas aeruginosa* | ATCC10145 | 7309001 | 79.1% |
| *Enterobacter cloacae* | ATCC13047T | 7308013 | 81% |
| *Streptococcus agalactiae* | ATCC13813 | 7701031 | 89.1% |
| *Klebsiella oxytoca* | ATCC13182T | 9211047 | 85.5% |
| *Citrobacter freundii* | ATCC29935T | 9410068 | 81.5% |
| *Salmonella typhimurium* | — | 9810059 | 71.3% |

The species having the highest score on the biochip is always the sought-after species; the score obtained is shown in the right-hand column.

The identification is correct for each of the species, demonstrating that the process of the present invention is effective on natural RNA samples as well as on RNA samples derived from an amplification technique.

What is claimed is:

1. A process for labeling a synthetic or natural ribonucleic acid (RNA), comprising:

fragmenting the RNA to produce a plurality of RNA fragments having freed terminal phosphates for further reaction, and labeling a plurality of said fragments at the terminal phosphates freed in the fragmentation step, located at the 3' end and/or the 5' end of said fragments.

2. The process according to claim 1, wherein the fragmentation and the labeling are effected in two steps.

3. The process according to claim 1, wherein the labeling of the 3' end or the 5' end of an RNA fragment is effected by binding a binding agent having a reactive function, which is linked to a label, or which is capable of being subsequently linked to a label, to the phosphate that is in the 2' position, in the 3' position or in the cyclic monophosphate 2'–3' position, with respect to the ribose.

4. The process according to claim 1, wherein the fragmentation and/or the labeling of the 3' end or the 5' end of an RNA fragment is effected by binding a binding agent having a nucleophilic, electrophilic or halide function, which is linked to a label, or which is capable of being subsequently linked to at least one label, to the phosphate in the 2' position, in the 3' position or in the cyclic monophosphate 2'–3' position, with respect to the ribose.

5. The process according to claim 1, wherein the fragmentation of the RNA is effected enzymically, chemically or physically.

6. The process according to claim 5, wherein the enzymic fragmentation of the RNA is carried out by means of nucleases.

7. The process according to claim 5, wherein the chemical fragmentation of the RNA is carried out by means of metal cations.

8. The process according to claim 5, wherein the physical fragmentation of the RNA is carried out by means of sonication or by means of radiation.

9. The process according to claim 1, wherein the labeling of the 3' end or the 5' end of an RNA fragment is effected by binding a molecule R—X, where R consists of the label and X is the agent for binding the label to the RNA, to the phosphate, which is linked to the 2' position, to the 3' position or to the cyclic monophosphate 2'–3' position of the ribose.

10. An RNA fragment that is obtained by the process according to claim 1, wherein the RNA fragment comprises, a single nucleotide which is labeled at the freed terminal phosphate that is located at the 3' end or the 5' end of the RNA fragment, and at least one other nucleotide whose base (purine: adenine/guanine or pyrimidine: uracil/cytosine) is identical to that of the labeled nucleotide, wherein the fragment comprises from 10 to 100 nucleotides.

11. An RNA fragment according to claim 10, wherein the RNA fragment comprises at least one thiophosphate nucleotide.

12. An RNA fragment according to claim 11, wherein the labeled nucleotide is a thiophosphate nucleotide.

13. An RNA fragment according to claim 10, wherein the fragment comprises from 30 to 70 nucleotides.

14. An RNA fragment according to claim 10, wherein the fragment comprises from 40 to 60 nucleotides.

15. The process according to claim 1, wherein the 3' end and/or the 5' end of each fragment is labeled, except that the original 3' end and the original 5' end of the starting RNA are not labeled.

16. The process of claim 7, wherein said metal cations are combined with a chemical catalyst.

17. The process according to claim 16, wherein the metal cations are $Mg^{++}$, $Mn^{++}$, $Cu^{++}$, $Co^{++}$ and/or $Zn^{++}$ ions and the chemical catalyst is an imidazole, a substituted analogue, or any chemical molecule that has an affinity for the RNA and that carries an imidazole nucleus or a substituted analogue.

18. The process according to claim 17, wherein the chemical catalyst is N-methylimidazole.

19. The process according to claim 9, wherein the agent for binding the label to the RNA is at least one member selected from the group consisting of hydroxyl, amine, hydrazine, alkoxylamine, alkyl halide, phenylmethyl halide, iodoacetamide and a maleimide grouping.

20. A method for detecting at least one nucleic acid selected from the group consisting of a DNA, a DNA fragment, an RNA, and an RNA fragment, comprising:

obtaining a sample containing said nucleic acid, and contacting said sample with an RNA fragment probe according to claim 13 to detect for said nucleic acid.

21. A method for binding a capture probe with a labeled target, comprising:

obtaining a sample containing said capture probe, and contacting said sample with a labeled RNA fragment according to claim 13, which is able to bind to said capture probe.

22. A process for labeling a synthetic or natural ribonucleic acid (RNA), comprising:

fragmenting the RNA to produce a plurality of RNA fragments having freed terminal phosphates for further reaction, and labeling with a label a plurality of said fragments at the terminal phosphates freed in the fragmentation step, located at the 3' end and/or the 5' end of said fragments, wherein the label is directly detectable.

23. The process of claim 22, wherein said label is horseradish peroxidase, alkaline phosphatase, β-galactosidase or glucose-6-phosphate dehydrogenase.

24. The process of claim 22, wherein said label is a fluorescent or luminescent compound or dye.

25. The process of claim 22, wherein said label is $^{32}P$, $^{35}S$ or $^{125}I$.

26. A process for labeling a synthetic or natural ribonucleic acid (RNA), comprising:

fragmenting the RNA to produce a plurality of RNA fragments having freed terminal phosphates for further reaction, and labeling with a label a plurality of said fragments at the terminal phosphates freed in the fragmentation step, located at the 3' end and/or the 5' end of said fragments, wherein the label is detectable by a physical, chemical or electrical characteristic of the label.

27. The process of claim 26, wherein the label is detectable by at least one of electron density, conductivity, amperometry, voltametry and impedance of the label.

28. The process of claim 26, wherein the label is detectable by diffraction, surface plasmon resonance, surface variation and angle of contact variation.

29. The process of claim 26, wherein the label is detectable by atomic force spectroscopy and the tunnel effect.

30. A process for labeling a synthetic or natural ribonucleic acid (RNA), comprising:

fragmenting the RNA to produce a plurality of RNA fragments having freed terminal phosphates for further reaction, and labeling a plurality of said fragments at said freed terminal phosphates located at the 3' end and/or the 5' end of the fragments, wherein the fragmentation and the labeling are effected in one step.

31. A process for labeling a natural ribonucleic acid (RNA), comprising:

fragmenting the natural RNA to produce a plurality of RNA fragments having freed terminal phosphates for further reaction, and labeling a plurality of said fragments at freed terminal phosphates located at the 3' end and/or the 5' end of said fragments.

32. The process of claim 31, wherein the fragmentation and the labeling are effected in at least two steps.

33. A process for labeling a synthetic or natural ribonucleic acid (RNA), comprising:

non-specifically fragmenting the RNA to produce a plurality of RNA fragments having freed terminal phosphates for further reaction, and labeling a plurality of said fragments at freed terminal phosphates located at the 3' end and/or the 5' end of said fragments.

34. The process of claim 22, wherein the label comprises at least one enzyme that produces a detectable signal.

35. The process of claim 22, wherein the label comprises at least one chromophore.

36. The process of claim 22, wherein the label comprises at least one radioactive molecule.

* * * * *